(12) United States Patent
Asaoka

(10) Patent No.: US 12,736,797 B2
(45) Date of Patent: Sep. 15, 2026

(54) ENDOSCOPE IMAGING DEVICE AND ENDOSCOPE IN WHICH DRIVE MALFUNCTION OF LENS DRIVE UNIT IS SUPPRESSED

(71) Applicant: FUJIFILM Corporation, Tokyo (JP)

(72) Inventor: Takuro Asaoka, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 295 days.

(21) Appl. No.: 18/423,328

(22) Filed: Jan. 26, 2024

(65) Prior Publication Data

US 2024/0302643 A1 Sep. 12, 2024

(30) Foreign Application Priority Data

Mar. 10, 2023 (JP) ................................ 2023-037175

(51) Int. Cl.

| | |
|---|---|
| ***G02B 23/24*** | (2006.01) |
| ***A61B 1/00*** | (2006.01) |
| ***H04N 23/54*** | (2023.01) |
| ***H04N 23/55*** | (2023.01) |
| *H04N 23/50* | (2023.01) |

(52) U.S. Cl.
CPC ........ *G02B 23/243* (2013.01); *A61B 1/00188* (2013.01); *H04N 23/54* (2023.01); *H04N 23/55* (2023.01); *H04N 23/555* (2023.01)

(58) Field of Classification Search
None
See application file for complete search history.

(56) References Cited

U.S. PATENT DOCUMENTS

| | | | | |
|---|---|---|---|---|
| 4,765,313 | A * | 8/1988 | Kumakura | A61B 1/00188 600/168 |
| 6,117,071 | A * | 9/2000 | Ito | A61B 1/05 600/129 |
| 9,737,200 | B2 * | 8/2017 | Makiyama | A61B 1/00163 |
| 2008/0167529 | A1 * | 7/2008 | Otawara | A61B 1/07 600/168 |
| 2009/0185032 | A1 * | 7/2009 | Sakai | F03G 7/0614 359/813 |

(Continued)

FOREIGN PATENT DOCUMENTS

| | | |
|---|---|---|
| JP | 2008110061 | 5/2008 |

*Primary Examiner* — John P Leubecker
(74) *Attorney, Agent, or Firm* — JCIPRNET

(57) ABSTRACT

An endoscope imaging device includes, on a distal end side, lenses that include a first movable lens movable along an optical axis direction, and a sensor capturing a subject image. The endoscope imaging device includes a lens accommodating portion accommodating the first movable lens, a housing disposed alongside the lens accommodating portion, a coupling portion coupling the lens accommodating portion and the housing to each other, a lens drive unit accommodated in the housing, a receiving portion provided at an end part of the housing or an end part of the lens accommodating portion, a pressing member provided at the end part of the lens accommodating portion or the end part of the housing facing the receiving portion and presses the lens accommodating portion or the housing, a first restricting portion restricting a position of the lens accommodating portion, and a second restricting portion restricting a position of the housing.

19 Claims, 8 Drawing Sheets

(56) References Cited

U.S. PATENT DOCUMENTS

| | | | | |
|---|---|---|---|---|
| 2009/0303619 | A1* | 12/2009 | Iwasaki | G02B 23/243 310/306 |
| 2010/0063361 | A1* | 3/2010 | Kuchimaru | G02B 23/2484 600/168 |
| 2012/0220828 | A1* | 8/2012 | Iwasaki | A61B 1/0051 600/109 |
| 2016/0353977 | A1* | 12/2016 | Kibayashi | A61B 1/00183 |
| 2017/0139198 | A1* | 5/2017 | Kibayashi | A61B 1/00045 |
| 2017/0265729 | A1* | 9/2017 | Wataya | A61B 1/00188 |
| 2017/0296042 | A1* | 10/2017 | Wataya | A61B 1/0011 |
| 2017/0296044 | A1* | 10/2017 | Wataya | H04N 23/55 |

* cited by examiner

ENDOSCOPE IMAGING DEVICE AND ENDOSCOPE IN WHICH DRIVE MALFUNCTION OF LENS DRIVE UNIT IS SUPPRESSED

CROSS-REFERENCE TO RELATED APPLICATIONS

The present application claims priority under 35 U.S.C. § 119 to Japanese Patent Application No. 2023-037175, filed on Mar. 10, 2023. The above application is hereby expressly incorporated by reference, in its entirety, into the present application.

BACKGROUND OF THE INVENTION

1. Field of the Invention

The present invention relates to an endoscope imaging device and an endoscope that acquire an image of an observation target, and particularly, to an endoscope imaging device and an endoscope that have an optical zooming function or a focusing function.

2. Description of the Related Art

A diagnosis and the like using an endoscope system that comprises an endoscope light source device, an endoscope (endoscopic scope), and a processor device have been widely performed.

An insertion part to be inserted into a body of a subject under examination is provided, and illumination light from the endoscope light source device passes through the insertion part and is emitted to an observation target. The endoscope images the observation target irradiated with illumination light through an imaging element to generate an image signal. The processor device generates an observation image to be displayed on a monitor by performing image processing on the image signal generated by the endoscope. The imaging element is electrically connected to a signal cable via a circuit board composed of a flexible wiring board or the like, and the signal cable is electrically connected to the processor device. In recent years, an endoscope having an optical zooming function or a focusing function has been proposed.

For example, JP2008-110061A describes an endoscope including an imaging unit that is inserted into a distal end portion and is fixed inside the distal end portion by a fixing member, a non-movable lens frame that is provided in the imaging unit and is in contact with the fixing member, and a movable lens frame that is provided inside the non-movable lens frame and is slidable along an inner surface of the non-movable lens frame, in which a notch portion is provided at a point symmetrical position through which an imaging optical axis of the imaging unit passes with respect to a fixed position by the fixing member and in at least one of portions where the distal end portion and the non-movable lens frame or the non-movable lens frame and the movable lens frame come into contact with each other. A moving object unit that performs a zooming function or a focusing function is coupled to the movable lens frame.

SUMMARY OF THE INVENTION

In JP2008-110061A described above, the movable lens frame comprises a movable lens, and the moving object unit is coupled to the movable lens frame. The movable lens frame is movable forward and backward in an imaging optical axis direction within a rear group lens frame that is the non-movable lens frame. The notch portion is provided to change a direction of a load acting on the rear group lens frame (non-movable lens frame) by the fixing member. However, the rear group lens frame (non-movable lens frame) is sandwiched from both sides between the fixing member and the notch portion. Therefore, in a case where the rear group lens frame (non-movable lens frame) is deformed, the movable lens frame cannot smoothly move forward and backward in the imaging optical axis direction, and the movement of the movable lens frame is restricted, which leads to drive malfunction in the moving object unit (lens drive unit).

An object of the present invention is to provide an endoscope imaging device and an endoscope in which drive malfunction of a lens drive unit is suppressed.

In order to achieve the above-described object, Invention [1] is an endoscope imaging device including, on a distal end side, a plurality of lenses that include a first movable lens which is movable along an optical axis direction, and a sensor that captures a subject image formed by the plurality of lenses, the endoscope imaging device comprising: a lens accommodating portion that accommodates the first movable lens which is movable along the optical axis direction among the plurality of lenses; a housing that is disposed alongside the lens accommodating portion as viewed from the optical axis direction; a coupling portion that couples the lens accommodating portion and the housing to each other in a state in which the lens accommodating portion and the housing communicate with each other; a lens drive unit that is accommodated in the housing; a receiving portion that is provided at an end part of the housing or an end part of the lens accommodating portion in an extension direction of the coupling portion as viewed from the optical axis direction; a pressing member that is provided at the end part of the lens accommodating portion or the end part of the housing facing the receiving portion in the extension direction and presses the lens accommodating portion or the housing; a first restricting portion that restricts a position of the lens accommodating portion in a cross direction crossing the extension direction of the coupling portion; and a second restricting portion that restricts a position of the housing in the cross direction crossing the extension direction of the coupling portion.

Invention [2] is the endoscope imaging device according to Invention [1], in which the first restricting portion is provided on both sides of the lens accommodating portion in the cross direction.

Invention [3] is the endoscope imaging device according to Invention [1] or [2], in which the second restricting portion is provided on both sides of the housing in the cross direction.

Invention [4] is the endoscope imaging device according to Invention [3], in which the pressing member is provided on an outer edge of the lens accommodating portion, within a range between a first point and a second point: the first point being, as viewed from the optical axis direction, a point at which a first straight line passing through a center point of the lens accommodating portion and a position within one of the second restricting portions, which is farthest from a straight line passing through the center point of the lens accommodating portion and a center point of the housing, where the second restricting portion effectively acts as a restriction for the position in the cross direction, intersects the outer edge of the lens accommodating portion provided on a side opposite to the housing with respect to the center point of the lens accommodating portion; and the second point being, as viewed from the optical axis direction, a point at which a second straight line passing through the center point of the lens accommodating portion and a position within the other of the second restricting portions, which is farthest from the straight line passing through the center point of the lens accommodating portion and the center point of the housing, where the second restricting portion effectively acts as a restriction for the position in the cross direction, intersects the outer edge of the lens accommodating portion provided on the side opposite to the housing with respect to the center point of the lens accommodating portion.

Invention [5] is the endoscope imaging device according to Invention [2], in which the pressing member is provided on an outer edge of the housing, within a range between a third point and a fourth point: the third point being, as viewed from the optical axis direction, a point at which a third straight line passing through a center point of the housing and a position within one of the first restricting portions, which is farthest from a straight line passing through a center point of the lens accommodating portion and the center point of the housing, where the first restricting portion effectively acts as a restriction for the position in the cross direction, intersects the outer edge of the housing provided on a side opposite to the lens accommodating portion with respect to the center point of the housing; and the fourth point being, as viewed from the optical axis direction, a point at which a fourth straight line passing through the center point of the housing and a position within the other of the first restricting portions, which is farthest from the straight line passing through the center point of the lens accommodating portion and the center point of the housing, where the first restricting portion effectively acts as a restriction for the position in the cross direction, intersects the outer edge of the housing provided on the side opposite to the lens accommodating portion with respect to the center point of the housing.

Invention [6] is the endoscope imaging device according to any one of Inventions [1] to [5], in which the receiving portion and the second restricting portion are continuously disposed along an outer edge of the housing.

Invention [7] is the endoscope imaging device according to any one of Inventions [1] to [6], in which the receiving portion and the first restricting portion are continuously disposed along an outer edge of the lens accommodating portion.

Invention [8] is the endoscope imaging device according to any one of Inventions [1] to [7], in which the extension direction of the coupling portion is a first direction that passes through a center point of the lens accommodating portion and a center point of the housing, as viewed from the optical axis direction, and the cross direction is a second direction orthogonal to the first direction within the same plane, as viewed from the optical axis direction.

Invention [9] is an endoscope comprising: the endoscope imaging device according to any one of Inventions [1] to [8].

According to the present invention, it is possible to provide an endoscope imaging device and an endoscope in which drive malfunction of a lens drive unit is suppressed.

DESCRIPTION OF THE PREFERRED EMBODIMENTS

Hereinafter, an endoscope imaging device and an endoscope of an embodiment of the present invention will be described in detail based on suitable embodiments shown in the accompanying drawings.

Note that the drawings to be described below are examples illustrating the present invention, and the present invention is not limited to the drawings shown below.

In the following description, "to" indicating a numerical range includes numerical values described on both sides thereof. For example, in a case where $\varepsilon$ is in a range of a numerical value $\varepsilon_\alpha$ to a numerical value $\varepsilon_\beta$, a range of $\varepsilon$ is a range including the numerical value $\varepsilon_\alpha$ and the numerical value $\varepsilon_\beta$ and is represented by $\varepsilon_\alpha \le \varepsilon \le \varepsilon_\beta$ in mathematical symbols.

In the following description, "specific angle", "parallel", "perpendicular", "orthogonal", and the like include error ranges generally allowed in the relevant technical field.

Endoscope System

An endoscope system irradiates an observation site, such as an inside of a subject's body, which is an observation target, with illumination light (not shown), images the observation site, generates a display image of the observation site based on an image signal obtained through the imaging, and displays the display image.

Figure 1:
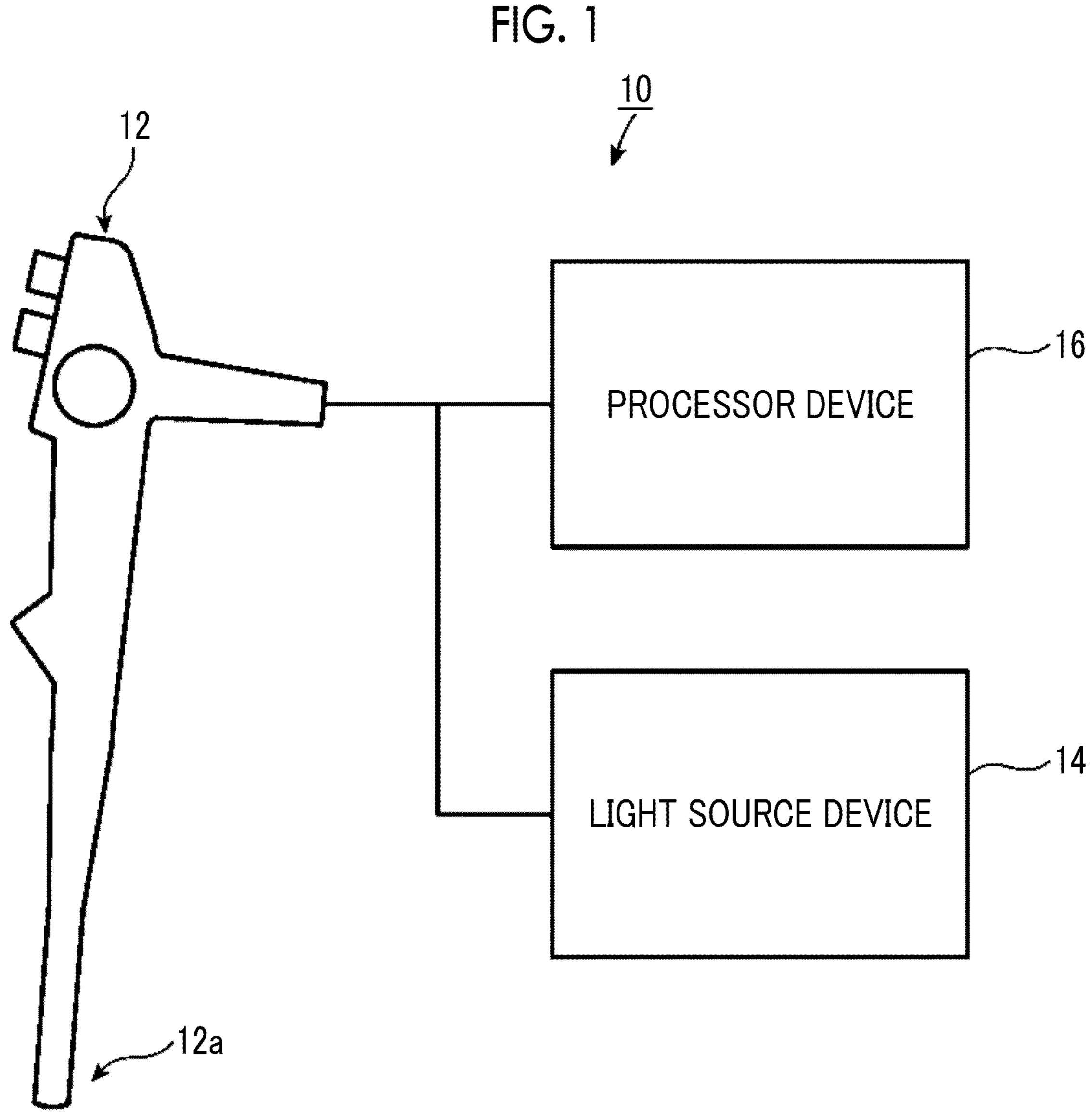
FIG. 1 is a schematic diagram showing an example of an endoscope system of an embodiment of the present invention.
Figure 2:
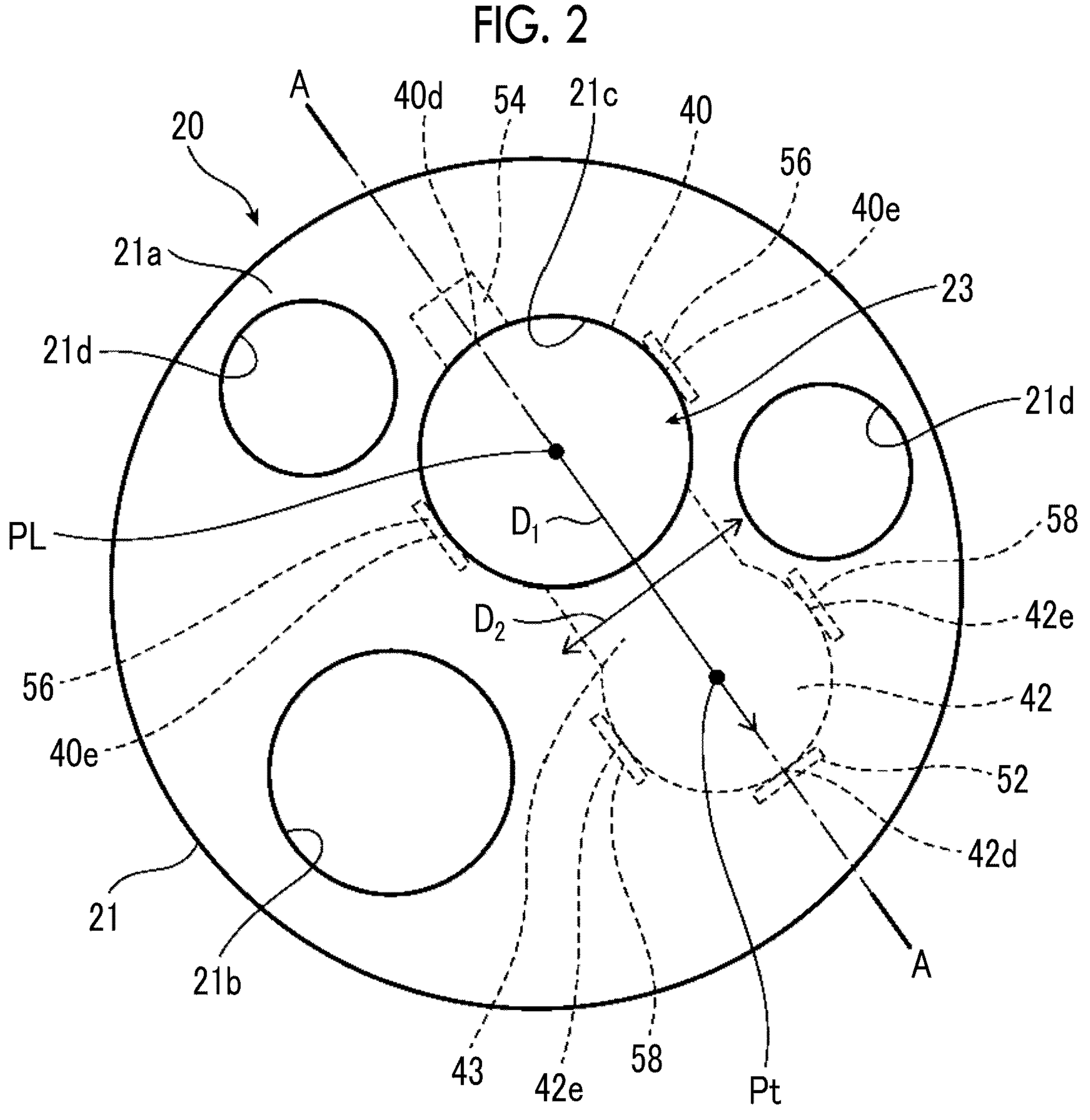
FIG. 2 is a schematic view showing a distal end surface of an example of an endoscope imaging device of the embodiment of the present invention.

FIG. 1 is a schematic diagram showing an example of the endoscope system of the embodiment of the present invention. FIG. 2 is a schematic view showing an example of a distal end surface of an example of the endoscope imaging device of the embodiment of the present invention. FIG. 2 is a schematic view of a distal end surface 21*a* of a distal end body 21 as viewed from an optical axis direction.

A receiving portion 52, a first restricting portion 56, and a second restricting portion 58, which will be described below, are each composed of a portion of the distal end body 21. However, in FIG. 2, thicknesses are exaggerated for illustration purposes to clearly show the receiving portion 52, the first restricting portion 56, and the second restricting portion 58.

An endoscope system 10 includes an endoscope 12, a light source device 14, and a processor device 16. The endoscope system 10 has the same configuration as a general endoscope except for a portion of an endoscope imaging device 20 (see FIG. 3) of the endoscope 12, which will be described below.

The endoscope system 10 may further comprise a water supply tank that stores washing water and the like, a suction pump that suctions a suction substance inside the body cavity (also including supplied washing water and the like), and the like. Furthermore, the endoscope system 10 may comprise a supply pump that supplies washing water inside the water supply tank or gases such as external air to a pipe line (not shown) inside the endoscope, and the like.

The endoscope 12, although not shown in detail, includes an insertion part that is inserted into the inside of the subject, an operation part that is contiguous to the insertion part, and a universal cord that extends from the operation part, and the insertion part is composed of a distal end portion, a bending portion that is contiguous to the distal end portion, and a soft portion that connects the bending portion and the operation part to each other.

A distal end portion 12*a* of the endoscope 12 is provided with an illumination optical system that emits illumination light for illuminating the observation site, a sensor and an imaging optical system that capture a subject image of the observation site, or the like. The bending portion is configured to bend in a direction orthogonal to a longitudinal axis of the insertion part, and a bending operation of the bending portion is operated at the operation part. In addition, the soft portion is configured to be relatively flexible to a deformable extent, along the shape of an insertion path of the insertion part.

The operation part is provided with a button for operating an imaging operation of the endoscope imaging device 20 (see FIG. 3) of the distal end portion 12*a*, a knob for operating the bending operation of the bending portion, or the like. In addition, the operation part is provided with an introduction port through which a treatment tool such as an electric scalpel is introduced, and a treatment tool channel that reaches the distal end portion from the introduction port and allows the treatment tool such as a forceps to be inserted is provided inside the insertion part.

A connector is provided at a terminal of the universal cord, and the endoscope 12 is connected to the light source device 14 that generates illumination light which is emitted from the illumination optical system of the distal end portion and to the processor device 16 that processes a video signal acquired by the endoscope imaging device 20 (see FIG. 3) of the distal end portion 12*a*, via the connector. At least one of signals or power is transmitted between the endoscope imaging device 20 (see FIG. 3) and the processor device 16 via an electrical cable group.

The processor device 16 generates video data of the observation site by processing the input video signal, and displays the generated video data on a monitor (not shown) or records the generated video data on a storage medium such as a hard disk. The processor device 16 may be composed of a processor such as a personal computer.

The light source device 14 is a light source device that is used to illuminate an observation target site inside the body cavity by generating illumination light, such as white light consisting of three primary color lights such as red light (R), green light (G), and blue light (B), or specific wavelength light, to supply the generated light to the endoscope 12, propagating the supplied light through a light guide or the like provided inside the endoscope 12, and emitting the propagated light from the illumination optical system of the distal end portion of the insertion part of the endoscope 12, in order to acquire the image signal of the observation target by imaging the observation target site inside the body cavity through the endoscope imaging device 20 (see FIG. 3) of the endoscope 12.

The light guide or the electrical cable group (signal cable) is accommodated inside the insertion part, the operation part, and the universal cord. The illumination light generated by the light source device 14 is guided to the illumination optical system of the distal end portion via the light guide, and light is emitted from the distal end surface 21*a* (see FIG. 2) of the endoscope imaging device 20 (see FIG. 3).

As shown in FIG. 2, the distal end surface 21*a* of the endoscope imaging device 20 is provided with, for example, a forceps port 21*b*, an observation window 21*c*, and a light guide 21*d*. Disposition positions of the forceps port 21*b*, the observation window 21*c*, and the light guide 21*d* on the distal end surface 21*a* are not particularly limited. In addition to these, an air and liquid supply nozzle (not shown) may be further provided on the distal end surface 21*a*.

A forceps pipe (not shown) is connected to the forceps port 21*b* integrally or separately. A forceps treatment tool, an injection needle, or the like is accommodated in the forceps pipe. The forceps treatment tool, the injection needle, or the like exits from the forceps port 21*b* to the outside. A forceps tube (not shown) is connected to the forceps pipe.

The observation window 21*c* is provided with a tubular lens accommodating portion 40 (see FIG. 3), which will be described below. In a case where the distal end surface 21*a* of the distal end body 21 is viewed from the optical axis direction, the tubular lens accommodating portion 40 and a tubular housing 42 are disposed side by side on the distal end body 21. The lens accommodating portion 40 and the housing 42 are coupled to each other in a state in which the lens accommodating portion 40 and the housing 42 communicate with each other through a coupling portion 43 in which two plate materials are disposed in parallel.

The light guide 21*d* is optically connected to the light source device 14 (see FIG. 1), guides illumination light emitted from the light source device 14, and emits the illumination light toward the observation target.

Example of Endoscope Imaging Device

Figure 3:
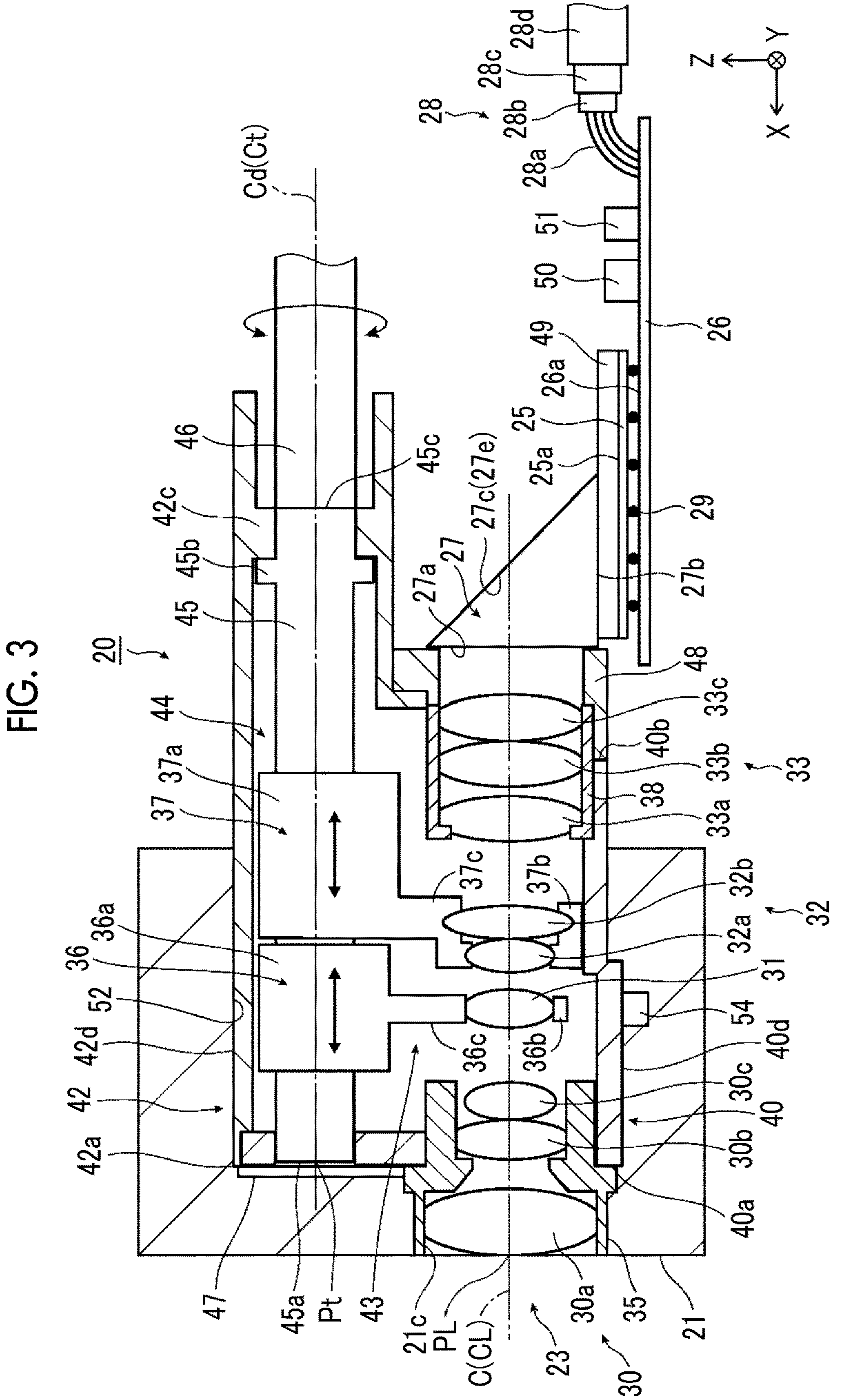
FIG. 3 is a schematic side cross-sectional view showing an example of the endoscope imaging device of the embodiment of the present invention.
Figure 4:
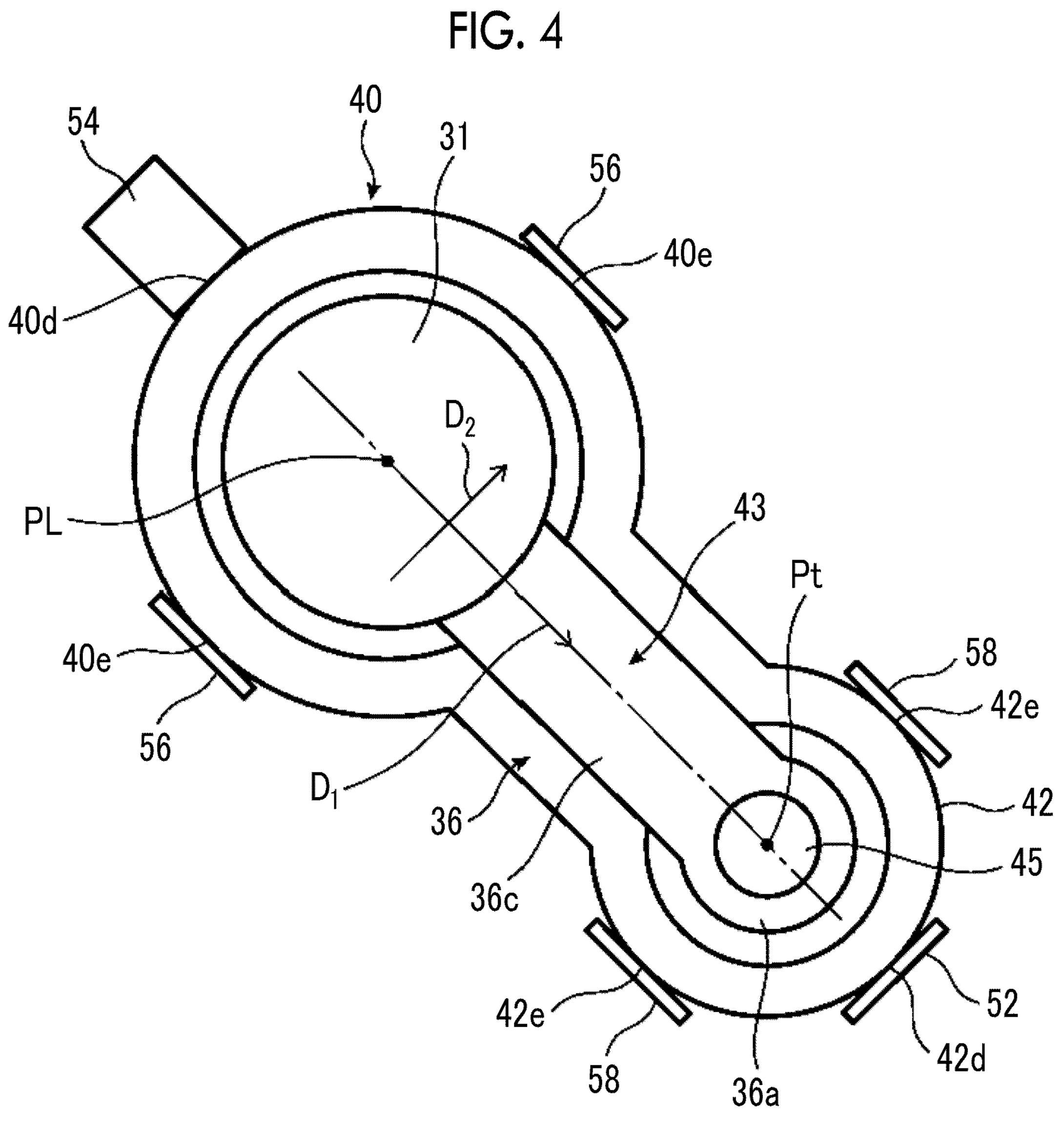
FIG. 4 is an enlarged schematic view showing disposition of a lens accommodating portion and a housing of an example of the endoscope imaging device of the embodiment of the present invention.

FIG. 3 is a schematic side cross-sectional view showing an example of the endoscope imaging device of the embodiment of the present invention. FIG. 4 is an enlarged schematic view showing disposition of the lens accommodating portion and the housing of an example of the endoscope imaging device of the embodiment of the present invention. FIG. 3 is a cross-sectional view corresponding to a cross-section taken along line A-A in FIG. 2.

FIG. 4 is a schematic view of the distal end surface 21*a* of the distal end body 21 as viewed from the optical axis direction. Moreover, in FIG. 4, thicknesses are exaggerated for illustration purposes to clearly show the receiving portion 52, the first restricting portion 56, and the second restricting portion 58. However, as described above, the receiving portion 52, the first restricting portion 56, and the second restricting portion 58 are each composed of a portion of the distal end body 21.

The endoscope imaging device 20 shown in FIG. 3 acquires an image of the observation target and has an optical zooming function or a focusing function.

The endoscope imaging device 20 comprises, on a distal end side, a plurality of lenses that includes a first movable lens 31 which is movable along the optical axis direction, and a sensor 25 that captures a subject image formed by the plurality of lenses. The plurality of lenses will be described below. Further, the endoscope imaging device 20 includes, for example, a circuit board 26, a prism 27, and a signal cable 28. The distal end side is a distal end body 21 side.

The endoscope imaging device 20 includes the lens accommodating portion 40 that accommodates the first movable lens 31 which is movable along the optical axis direction among the plurality of lenses, the housing 42 that is disposed alongside the lens accommodating portion 40 as viewed from the optical axis direction as described above, the coupling portion 43 that couples the lens accommodating portion 40 and the housing 42 to each other in a state in which the lens accommodating portion 40 and the housing 42 communicate with each other.

In addition, the endoscope imaging device 20 includes a lens drive unit 44 that moves the lens which is movable along an optical axis C, within an imaging lens 23 for exhibiting the optical zooming function or the focusing function, along the optical axis C. Being movable along the optical axis C means being movable in the optical axis direction.

Here, a direction parallel to the optical axis C of the imaging lens 23 is denoted by an X direction. Among two directions orthogonal to the optical axis C, one is denoted by a Y direction, and the remaining one is denoted by a Z direction. The above-described X direction corresponds to the optical axis direction. A direction of an axis such as the optical axis direction refers to an extension direction of the axis. The optical axis direction is an extension direction of the optical axis C.

The imaging lens 23 is an optical element that forms an image of light incident on the imaging lens 23 on a light-receiving surface 25*a* of the sensor 25. The imaging lens 23 forms the subject image on the light-receiving surface 25*a* of the sensor 25.

The imaging lens 23 includes the plurality of lenses including the first movable lens 31 that is movable along the optical axis C. The imaging lens 23 includes, for example, an objective lens 30, the first movable lens 31, a second movable lens 32, and a stationary lens 33. The objective lens 30, the first movable lens 31, the second movable lens 32, and the stationary lens 33 are disposed in order from the distal end side of the endoscope imaging device 20 with their optical axes C of the lenses aligned with each other. The stationary lens 33 is disposed on a sensor 25 side. The distal end side of the endoscope imaging device 20 is a subject side.

The objective lens 30 includes, for example, three lenses 30*a*, 30*b*, and 30*c*. The three lenses 30*a*, 30*b*, and 30*c* are collectively held by one lens holding member 35.

The first movable lens 31 is, for example, one lens. The first movable lens 31 is held by a first movable lens holding portion 36. The first movable lens holding portion 36 includes a tubular guide portion 36*a*, a lens frame 36*b*, and a coupling portion 36*c* that couples the guide portion 36*a* and the lens frame 36*b* to each other, and the guide portion 36*a*, the lens frame 36*b*, and the coupling portion 36*c* are integrally formed. More specifically, the above-described first movable lens 31 is held by the lens frame 36*b*.

The second movable lens 32 includes, for example, two lenses 32*a* and 32*b*. The two lenses 32*a* and 32*b* of the second movable lens 32 are held by a second movable lens holding portion 37. The second movable lens holding portion 37 includes a tubular guide portion 37*a*, a lens frame 37*b*, and a coupling portion 37*c* that couples the guide portion 37*a* and the lens frame 37*b* to each other, and the guide portion 37*a*, the lens frame 37*b*, and the coupling portion 37*c* are integrally formed. More specifically, the two lenses 32*a* and 32*b* of the above-described second movable lens 32 are collectively held by one lens frame 37*b*.

The stationary lens 33 includes, for example, three lenses 33*a*, 33*b*, and 33*c*. The three lenses 33*a*, 33*b*, and 33*c* are collectively held by one stationary lens holding member 38.

The imaging lens 23 is accommodated in the lens accommodating portion 40. The lens accommodating portion 40 has a tubular shape. For example, a central axis CL of the lens accommodating portion 40 and the optical axis C of the imaging lens 23 are disposed to coincide with each other.

As described above, the housing 42 is provided alongside the lens accommodating portion 40. As shown in FIG. 3, the lens accommodating portion 40 and the housing 42 communicate with each other through the coupling portion 43. For example, the central axis CL of the lens accommodating portion 40 and a central axis Ct of the housing 42 are disposed to be parallel to each other.

In a case where the lens accommodating portion 40, the housing 42, and the coupling portion 43 are viewed from the distal end surface 21*a* of the endoscope imaging device 20, two circles, which are spaced apart from each other, are connected by two parallel edges such that centers of the two circles are positioned between the two edges, and have a shape that does not include circular arcs inside the two edges. In other words, the circular arcs are connected to both sides of the two parallel edges, and the shape is composed of the circular arcs except for the two edges.

The above-described lens holding member 35 is fitted into a subject-side end surface 40*a* of the lens accommodating portion 40. In FIG. 3, the subject-side end surface 40*a* of the lens accommodating portion 40 and a subject-side end surface 42*a* of the housing 42 are on the same plane in the optical axis direction, but the lens holding member 35 protrudes from the subject-side end surface 40*a* of the lens accommodating portion 40. The lens 30*a* of the objective lens 30 is disposed outside the lens accommodating portion 40.

The imaging lens 23 is held such that the optical axis C of the imaging lens 23 is perpendicular to an incidence surface 27*a* of the prism 27, which will be described below. It should be noted that the configuration of the imaging lens 23 is not particularly limited to the above-described configuration. In addition, each lens constituting the imaging lens 23 may be a convex lens or a concave lens.

The lens drive unit 44 is accommodated in the housing 42. The lens drive unit 44 includes a cam shaft 45, and the first movable lens holding portion 36 and the second movable lens holding portion 37, which are described above. For example, the cam shaft 45 has a columnar shape, and a rotation axis Cd thereof is disposed to coincide with the central axis Ct of the housing 42. From this, the central axis CL of the lens accommodating portion 40 and the central axis Ct of the housing 42 are parallel to the optical axis C.

A drive member 46 is connected to an end part 45*c* of the cam shaft 45 provided on a side opposite to the above-described end surface 42*a*. The cam shaft 45 rotates about the rotation axis Cd with the rotation of the drive member 46.

The drive member 46 is connected to, for example, a drive unit such as a motor. The drive member 46 is rotated by the motor. In addition, for example, the drive member 46 is composed of a member having flexibility. More specifically, the drive member 46 is composed of a wire.

A distal end support portion 47 is provided on the subject-side end surface 42*a* of the housing 42. The cam shaft 45 is rotatably supported by the distal end support portion 47.

The cam shaft 45 includes a flange 45*b* that is provided in the vicinity of the end part 45*c* and that protrudes outward along an outer periphery. A locking ring 42*c* provided on the side opposite to the above-described end surface 42*a* is provided inside the housing 42 in which the lens drive unit 44 is accommodated.

The flange 45*b* of the cam shaft 45 is disposed on an end surface 42*a* side of the housing 42 with respect to the locking ring 42*c* and is accommodated inside the housing 42. The friction between the flange 45*b* of the cam shaft 45 and the locking ring 42*c* is small and does not hinder the rotation of the cam shaft 45. In addition, the locking ring 42*c* prevents the cam shaft 45 from coming out.

The cam shaft 45 is provided with the first movable lens holding portion 36 and the second movable lens holding portion 37 between a distal end 45*a* and the flange 45*b* in a rotation axis direction. The first movable lens holding portion 36 and the second movable lens holding portion 37 are disposed across the lens accommodating portion 40, the coupling portion 43, and the housing 42.

For example, a first cam groove (not shown) for moving the first movable lens 31 along the optical axis direction and a second cam groove (not shown) for moving the second movable lens 32 along the optical axis direction are provided on an outer peripheral surface of the cam shaft 45 between the distal end 45*a* and the flange 45*b* described above. The rotation axis direction is a direction parallel to the optical axis direction.

The cam shaft 45 is slidably inserted into the guide portion 36*a* of the first movable lens holding portion 36. The guide portion 36*a* of the first movable lens holding portion 36 is provided with a cam pin (not shown) that is engaged with the first cam groove (not shown).

In addition, the cam shaft 45 is slidably inserted into the guide portion 37*a* of the second movable lens holding portion 37. The guide portion 37*a* of the second movable lens holding portion 37 is provided with a cam pin (not shown) that is engaged with the second cam groove (not shown).

In a case where the cam shaft 45 rotates in a state in which the cam pin (not shown) of the first movable lens holding portion 36 is engaged with the first cam groove (not shown), the first movable lens holding portion 36 moves along the rotation axis direction (the optical axis direction) of the cam shaft 45 according to the direction of the rotation. Further, the first movable lens holding portion 36 can be stopped and positioned at a predetermined position in the rotation axis direction (optical axis direction) of the cam shaft 45. In this case, the coupling portion 36*c* of the first movable lens holding portion 36 passes through the coupling portion 43, and the first movable lens 31 moves along the rotation axis direction (optical axis direction) of the cam shaft 45 and is positioned at a predetermined position.

In a case where the cam shaft 45 rotates in a state in which the cam pin (not shown) of the second movable lens holding portion 37 is engaged with the second cam groove (not shown), the second movable lens holding portion 37 moves along the rotation axis direction (optical axis direction) of the cam shaft 45 according to the direction of the rotation. Further, the second movable lens holding portion 37 can be stopped and positioned at a predetermined position in the rotation axis direction (optical axis direction) of the cam shaft 45. In this case, the coupling portion 37*c* of the second movable lens holding portion 37 passes through the coupling portion 43, and the second movable lens 32 moves along the rotation axis direction (optical axis direction) of the cam shaft 45 and is positioned at a predetermined position.

In this manner, the first movable lens 31 and the second movable lens 32 can be moved along the optical axis direction, and zooming imaging and focusing can be performed by changing the focal length of the imaging lens 23.

The sensor 25 is a sensor that captures the subject image by converting light of which the image is formed by the imaging lens 23 into an electrical signal through photoelectric conversion, and includes the light-receiving surface 25*a*. In the sensor 25, the light of which the image is formed by the imaging lens 23, that is, imaging light of the observation target, is incident on the light-receiving surface 25*a*, and the imaging light is photoelectrically converted, thereby capturing the subject image. The sensor 25 is, for example, a conventionally known photoelectric conversion element, and a charge coupled device (CCD) type image sensor or a complementary metal oxide semiconductor (CMOS) image sensor can be used.

The sensor 25 is disposed on an end part 40*b* side of the lens accommodating portion 40 provided on a side opposite to the subject side. As shown in FIG. 3, the sensor 25 is electrically connected to a front surface 26*a* of the circuit board 26, for example, via a bump 29 having conductivity. In addition, as shown in FIG. 3, the sensor 25 is mounted on the circuit board 26 such that the light-receiving surface 25*a* is parallel to the optical axis C of the imaging lens 23. The mounting refers to electrical connection.

An underfill layer (not shown) for firmly connecting the sensor 25 and the circuit board 26 to each other can also be provided between the sensor 25 and the circuit board 26.

The bump 29 is made of a metal or an alloy. More specifically, the bump 29 is made of solder. The bump 29 formed of solder is also referred to as a solder ball. The bump 29 is not limited to the solder or the like as long as the sensor 25 and the circuit board 26 can be electrically connected to each other. In addition, the sensor 25 and the circuit board 26 may be electrically connected directly to each other.

Further, the underfill layer mitigates a stress generated at a junction portion between the sensor 25 and the circuit board 26, for example, at the bump 29, due to the difference in thermal expansion coefficients between the sensor 25 and the circuit board 26. With the underfill layer, the sensor 25 and the circuit board 26 are firmly connected to each other, and the reliability of the electrical connection is increased, so that the endoscope imaging device 20 having high reliability can be obtained.

An underfill agent that constitutes the underfill layer is not particularly limited, and an underfill agent that is used as a sealing resin between the sensor 25 and the circuit board 26 can be appropriately used. For example, a one-pack heat-curable type epoxy resin is used as the underfill agent. In this case, the underfill agent is supplied, and then is heated and held at a predetermined temperature, thereby forming the underfill layer.

The circuit board 26 is a substrate on which the sensor 25 is mounted. In addition, in the circuit board 26, for example, electronic components 50 and 51 are mounted on the front surface 26*a* of the circuit board 26, in addition to the sensor 25. The electronic components 50 and 51 are components for driving the sensor 25 and are not particularly limited, and examples thereof include a voltage regulator, a resistor, and a capacitor. The voltage regulator is a device that stabilizes a voltage to the sensor 25, and outputs a constant voltage to the sensor 25.

In the example shown in the drawing, the circuit board 26 has a flat plate shape, but the present invention is not limited thereto.

The circuit board 26 is composed of, for example, a printed wiring board, but may be composed of a substrate having flexibility. In this case, the circuit board 26 is composed of, for example, a flexible printed board.

In addition, a plurality of connection terminals (not shown) through which signals or power is input and output with respect to the sensor 25 and the electronic components 50 and 51 are provided on the front surface 26*a* of the circuit board 26. A signal line 28*a* of the signal cable 28 is electrically connected to the connection terminal. As a result, the sensor 25 and the signal cable 28 are electrically connected to each other. Light is converted into the electrical signal by the sensor 25, and this electrical signal is transmitted via the signal cable 28. The signal cable 28 is inserted into the insertion part, the operation part, the universal cord, and the like of the endoscope and is electrically connected to the processor device 16 (see FIG. 1).

The configuration of the signal cable 28 is not particularly limited. For example, as shown in FIG. 3, the signal cable 28 includes a plurality of the signal lines 28*a*, a covering layer 28*b* that covers each signal line 28*a*, a shield conductor 28*c* provided around the entire circumference of the plurality of signal lines 28*a* covered with the covering layer 28*b*, and an outer sheath 28*d* that covers the shield conductor 28*c*. The signal cable 28 is a multi-core cable in which the plurality of signal lines 28*a* are bundled, the shield conductor 28*c* is provided around the plurality of signal lines 28*a*, and the plurality of signal lines 28*a* are accommodated inside the cylindrical outer sheath 28*d*.

The outer sheath 28*d* constitutes the outer periphery of the signal cable 28. The covering layer 28*b*, the shield conductor 28*c*, and the outer sheath 28*d* each have, for example, a cylindrical shape. Additionally, the shield conductor 28*c* of the signal cable 28 is referred to as a shield. The signal cable 28 includes, for example, five signal lines 28*a*. The number of the signal lines 28*a* depends on the configuration of the endoscope imaging device 20, is not particularly limited, and may be two, three, four, or six or more.

The prism 27 guides light that has passed through the imaging lens 23 to the light-receiving surface 25*a* of the sensor 25. The prism 27 is, for example, a right-angle prism in which the incidence surface 27*a* and an emission surface 27*b* are orthogonal to each other. In addition, the prism 27 includes an inclined surface 27*c* connecting the incidence surface 27*a* and the emission surface 27*b* to each other. The inclined surface 27*c* is a reflecting surface 27*e* of the prism 27.

The prism 27 is held by a prism holding portion 48 provided at an end part 40*b* of the lens accommodating portion 40 on the side opposite to the subject side. The prism 27 is disposed such that the incidence surface 27*a* faces the lens 33*c* of the stationary lens 33. In addition, the prism 27 is disposed such that the emission surface 27*b* faces the light-receiving surface 25*a* of the sensor 25.

Further, for example, a cover glass 49 is disposed between the emission surface 27*b* of the prism 27 and the light-receiving surface 25*a* of the sensor 25. The cover glass 49 protects the light-receiving surface 25*a* of the sensor 25. The prism 27 and the cover glass 49 are bonded with, for example, a photocurable adhesive. A configuration may be employed in which the cover glass 49 is not provided.

The prism 27 bends light that has passed through the imaging lens 23 on the inclined surface 27*c*, that is, on the reflecting surface 27*e*, by, for example, 90° to change an optical path, and guides the light to the light-receiving surface 25*a* of the sensor 25. The light transmitted through the imaging lens 23 is incident on the prism 27, is reflected on the inclined surface 27*c* of the prism 27, that is, on the reflecting surface 27*e*, and is incident on the light-receiving surface 25*a* of the sensor 25. The light transmitted through the imaging lens 23 is light including information on the observation target.

In the endoscope imaging device 20, an observational image captured by the sensor 25 from the imaging lens 23 is formed on the light-receiving surface 25*a* of the sensor 25 and converted into the electrical signal, and this electrical signal is output to the processor device 16 (see FIG. 1) via the signal cable 28 and is converted into the video signal, and an observation image is displayed on the monitor connected to the processor device 16.

As shown in FIG. 2, the endoscope imaging device 20 includes the receiving portion 52 that is provided at an end part 42*d* of the housing 42 or an end part 40*d* of the lens accommodating portion 40 in the extension direction of the coupling portion 43 in a case where the distal end surface 21*a* of the distal end body 21 is viewed from the optical axis direction. In a case where the distal end body 21 is viewed from the optical axis direction, for example, the extension direction of the coupling portion 43 is a direction in which two parallel plate materials constituting the coupling portion 43 extend. More specifically, the extension direction of the coupling portion 43 is a first direction $D_1$ passing through a center point PL of the lens accommodating portion 40 and a center point Pt of the housing 42.

In the endoscope imaging device 20, as shown in FIG. 2, the receiving portion 52 is provided at a position of the end part 42*d* of the housing 42 in the first direction $D_1$ or the end part 40*d* of the lens accommodating portion 40 in the first direction $D_1$ passing through the center point PL of the lens accommodating portion 40 and the center point Pt of the housing 42 in a case where the distal end surface 21*a* of the distal end body 21 is viewed from the optical axis direction.

Here, the center point PL is a point at which the central axis CL of the lens accommodating portion 40 passes through the lens accommodating portion 40 in a case where the distal end surface 21*a* of the distal end body 21 is viewed from the optical axis direction. The center point Pt is a point at which the central axis Ct of the housing 42 passes through the housing 42 in a case where the distal end surface 21*a* of the distal end body 21 is viewed from the optical axis direction.

As shown in FIG. 2, the endoscope imaging device 20 includes a pressing member 54 that is provided at the end part 40*d* of the lens accommodating portion 40 or the end part 42*d* of the housing 42 facing the receiving portion 52 in the extension direction and that presses the lens accommodating portion 40 or the housing 42 in a case where the distal end surface 21*a* of the distal end body 21 is viewed from the optical axis direction.

More specifically, the pressing member 54 that presses the lens accommodating portion 40 is provided at the end part 40*d* of the lens accommodating portion 40 or the end part 42*d* of the housing 42 facing the receiving portion 52 in the first direction $D_1$.

As shown in FIGS. 2 and 4, the receiving portion 52 is provided at a position of the end part 42*d* of the housing 42 in the first direction $D_1$. The pressing member 54 that presses the lens accommodating portion 40 is provided at the end part 40*d* of the lens accommodating portion 40.

The receiving portion 52 receives a pushing force that acts on the receiving portion 52 in the extension direction, for example, a pressing force that acts in the first direction $D_1$, from the pressing member 54 to restrict positions of the lens accommodating portion 40 and the housing 42 in the first direction $D_1$. The pressing member 54 is, for example, a screw.

The receiving portion 52 is a portion of the distal end body 21 and is composed of, for example, a contact portion or a contact surface between the housing 42 and the distal end body 21. Therefore, the receiving portion 52 may have a linear shape or a circular arc shape along an outer edge of the housing 42 in a case where the distal end surface 21*a* of the distal end body 21 is viewed from the optical axis direction.

The endoscope imaging device 20 includes the first restricting portion 56 that restricts the position of the lens accommodating portion 40 in a cross direction crossing the extension direction of the coupling portion 43. The first restricting portion 56 may be provided on both sides of the lens accommodating portion 40 in the cross direction or may be provided on any one of both sides of the lens accommodating portion 40 in the cross direction.

In addition, the endoscope imaging device 20 includes the second restricting portion 58 that restricts the position of the housing 42 in the cross direction crossing the extension direction of the coupling portion 43. The second restricting portion 58 may be provided on both sides of the housing 42 in the cross direction or may be provided on any one of both sides of the housing 42 in the cross direction.

Here, the cross direction crossing the extension direction of the coupling portion 43 is a second direction $D_2$ orthogonal to the first direction $D_1$ within the same plane as the first direction $D_1$, that is, within the distal end surface 21*a* of the distal end body 21.

More specifically, as shown in FIGS. 2 and 4, the lens accommodating portion 40 includes the first restricting portion 56 that is provided on both sides in the second direction $D_2$ orthogonal to the first direction $D_1$, for example, on side end parts 40*e*, and that restricts the position of the lens accommodating portion 40 in the second direction $D_2$. The side end part 40*e* includes a most projecting position of the lens accommodating portion 40 in the second direction $D_2$. As described above, the first restricting portion 56 may be provided on any one of both sides of the lens accommodating portion 40 in the second direction $D_2$.

The housing 42 includes the second restricting portion 58 that is provided on both sides in the second direction $D_2$, for example, on side end parts 42*e*, and that restricts the position of the housing 42 in the second direction $D_2$. The side end part 42*e* includes a most projecting position of the housing 42 in the second direction $D_2$. As described above, the second restricting portion 58 may be provided on any one of both sides of the housing 42 in the second direction $D_2$.

The first restricting portion 56 is a portion of the distal end body 21 and is composed of, for example, a contact portion or a contact surface between the lens accommodating portion 40 and the distal end body 21. Therefore, the first restricting portion 56 may have a linear shape or a circular arc shape along an outer edge of the lens accommodating portion 40 in a case where the distal end surface 21*a* of the distal end body 21 is viewed from the optical axis direction.

The second restricting portion 58 is a portion of the distal end body 21 and is composed of, for example, a contact portion or a contact surface between the housing 42 and the distal end body 21. Therefore, the second restricting portion 58 may have a linear shape or a circular arc shape along an outer edge of the housing 42 in a case where the distal end surface 21*a* of the distal end body 21 is viewed from the optical axis direction.

As shown in FIG. 4, the lens accommodating portion 40, the coupling portion 43, and the housing 42 are fixed to the distal end body 21 by sandwiching the lens accommodating portion 40 and the housing 42 between the receiving portion 52 and the pressing member 54 in the extension direction of the coupling portion 43, for example, in the first direction $D_1$, in a state in which the position of the lens accommodating portion 40 in the second direction $D_2$ is restricted by the first restricting portions 56 and the position of the housing 42 in the second direction $D_2$ is restricted by the second restricting portions 58. In this state, a force acting on the coupling portion 43 in the cross direction crossing the extension direction of the coupling portion 43, for example, on a second direction $D_2$ side, due to the pressing force of the pressing member 54 deforms the coupling portion 43. In this case, the clearance of the first movable lens holding portion 36 increases because the coupling portion 43 is deformed to be opened in the cross direction, for example, in the second direction $D_2$. From this, the movement of the first movable lens 31 in the optical axis direction by the lens drive unit 44 is not hindered, and drive malfunction of the first movable lens 31 is suppressed. In addition, the clearance also increases for the second movable lens holding portion 37 as in the above-described first movable lens holding portion 36, so that drive malfunction of the second movable lens 32 by the lens drive unit 44 is suppressed. In this way, drive malfunction of the lens movable along the optical axis C by the lens drive unit 44 is suppressed.

Figure 5:
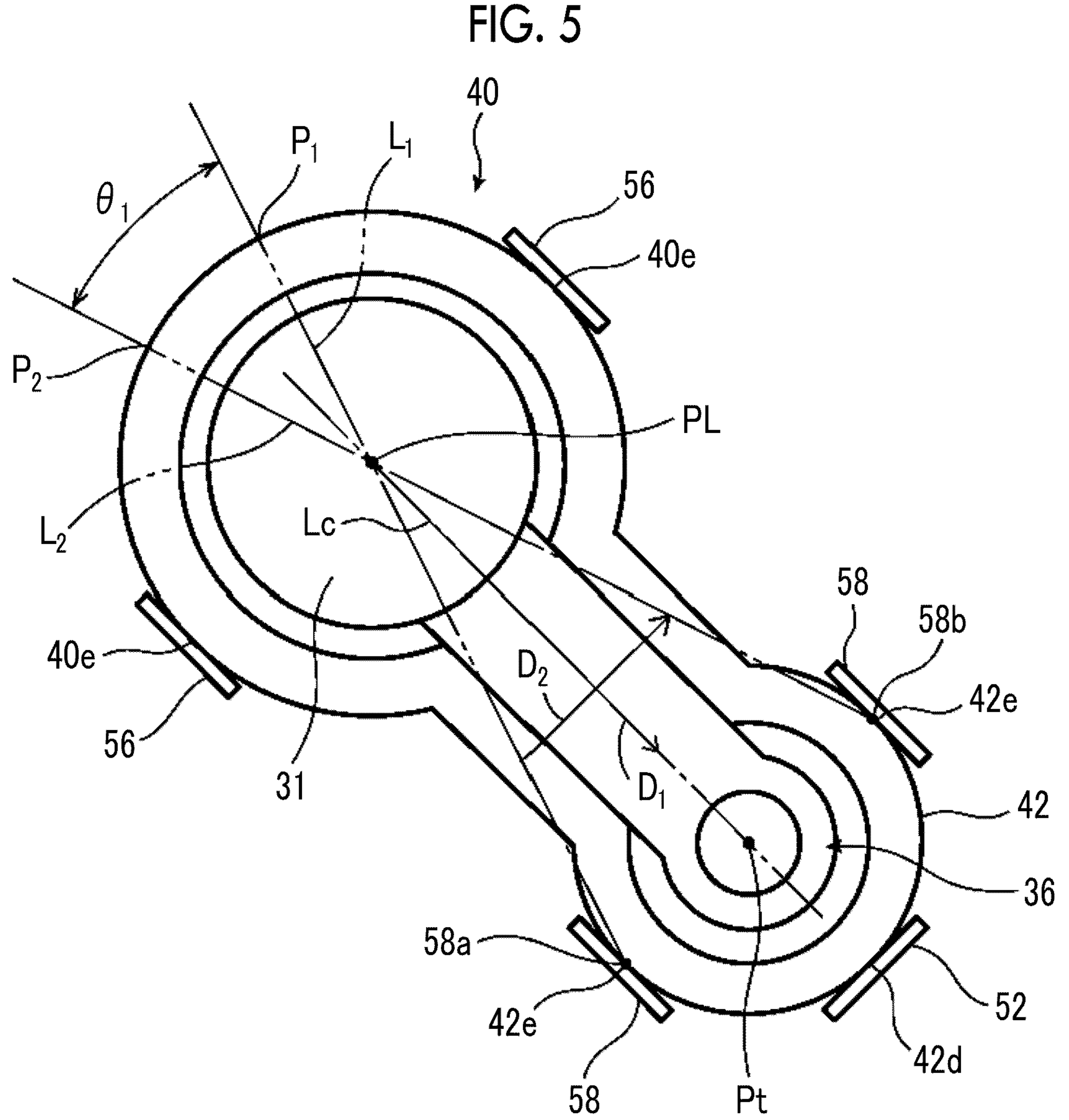
FIG. 5 is a schematic view illustrating disposition of a pressing member of the endoscope imaging device of the embodiment of the present invention.
Figure 6:
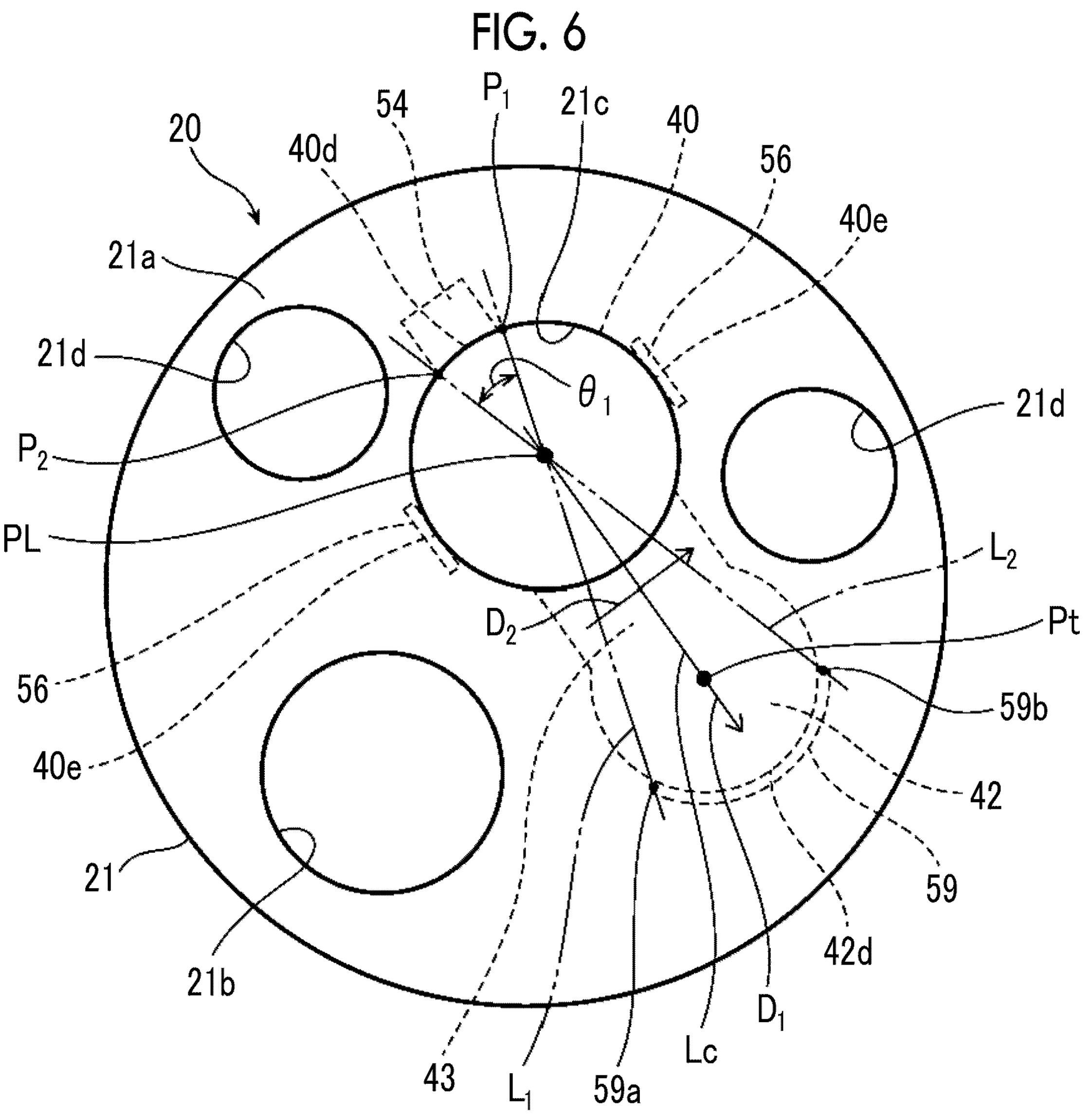
FIG. 6 is a schematic view showing another example of the distal end surface of an example of the endoscope imaging device of the embodiment of the present invention.
Figure 7:
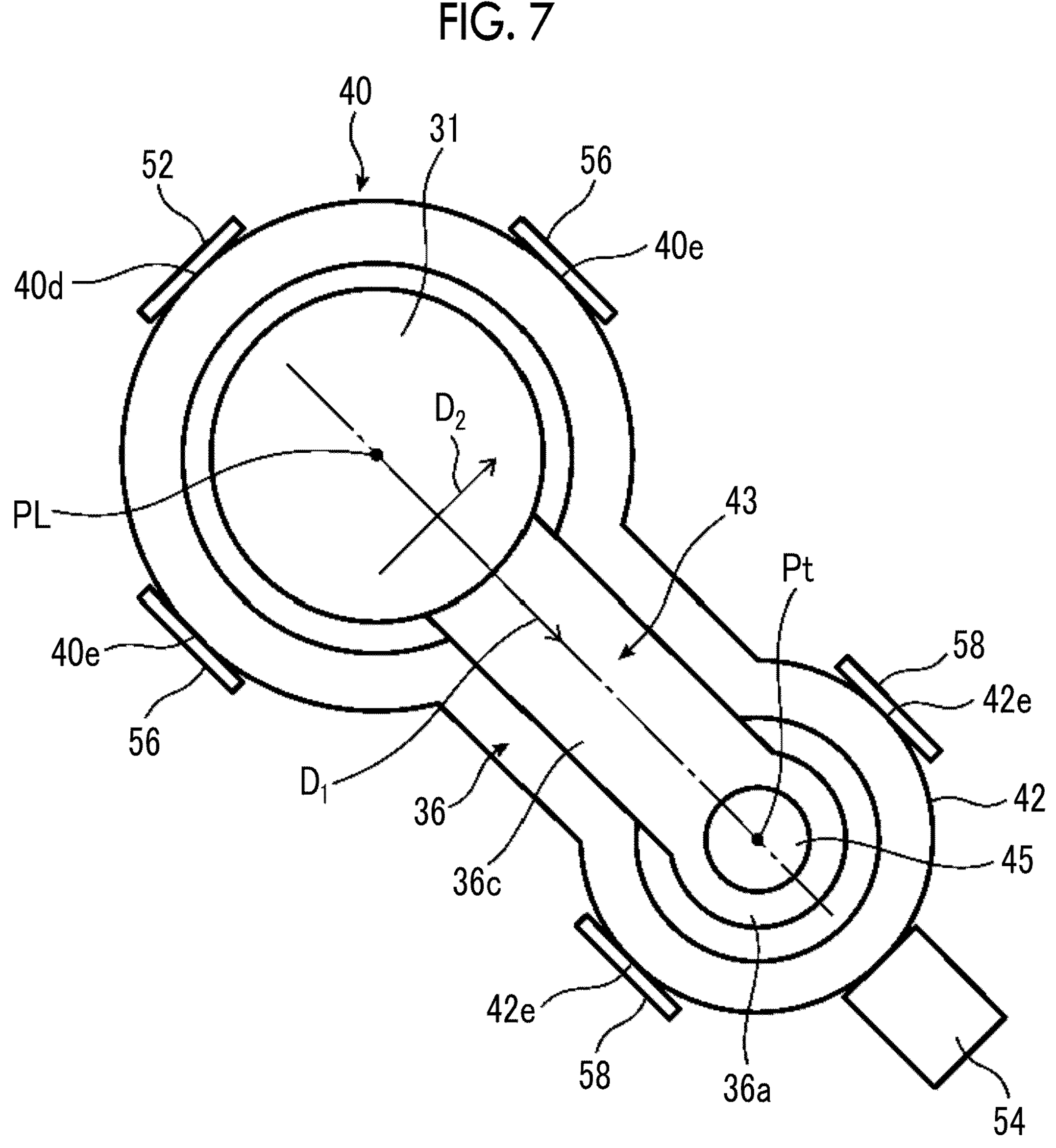
FIG. 7 is a schematic view showing another example of the disposition of the pressing member of the endoscope imaging device of the embodiment of the present invention.
Figure 8:
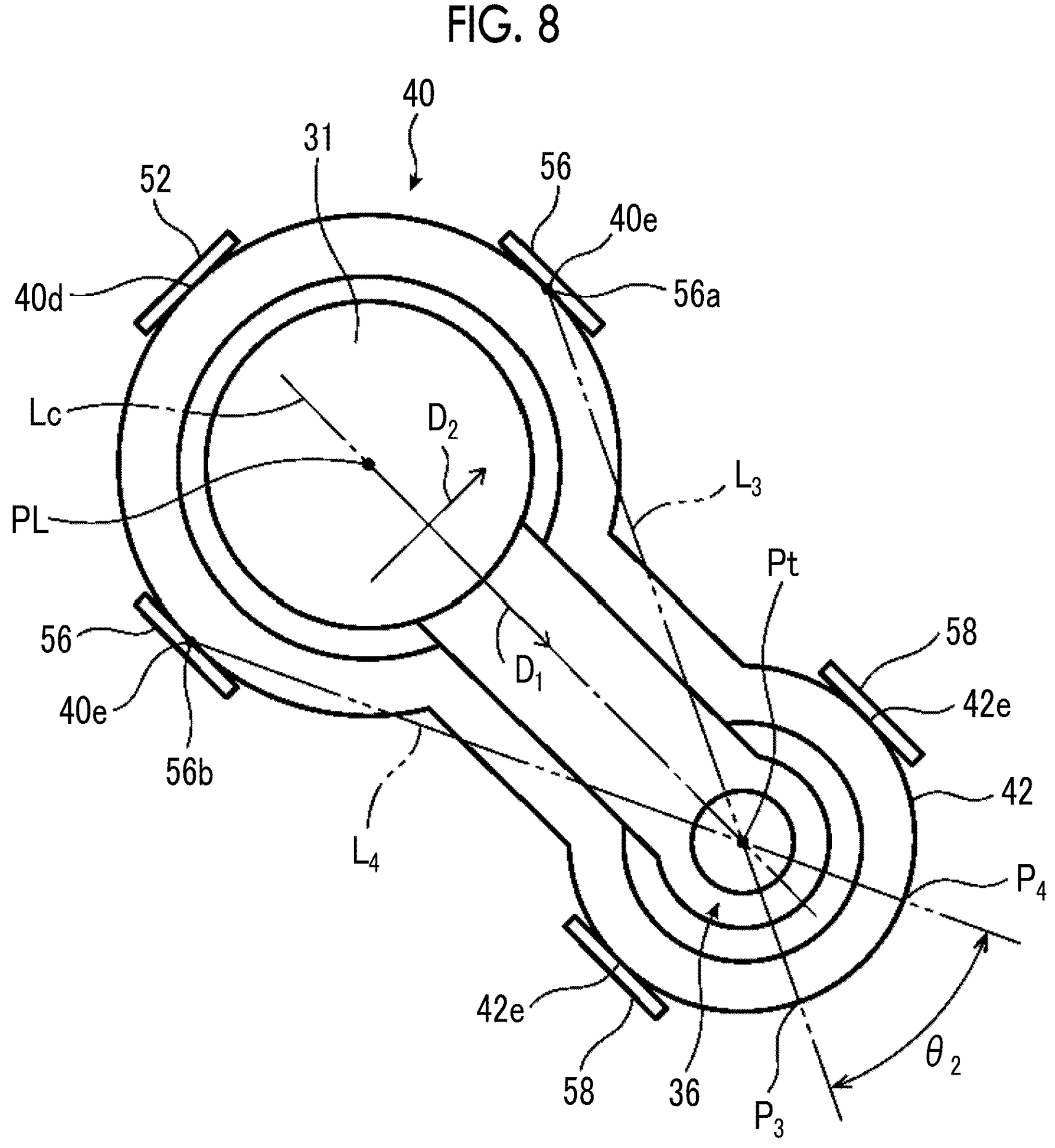
FIG. 8 is a schematic view illustrating the disposition of the pressing member of the endoscope imaging device of the embodiment of the present invention.

Here, FIG. 5 is a schematic view illustrating the disposition of the pressing member of the endoscope imaging device of the embodiment of the present invention. FIG. 6 is a schematic view showing another example of the distal end surface of an example of the endoscope imaging device of the embodiment of the present invention. FIG. 7 is a schematic view showing another example of the disposition of the pressing member of the endoscope imaging device of the embodiment of the present invention. FIG. 8 is a schematic view illustrating the disposition of the pressing member of the endoscope imaging device of the embodiment of the present invention.

In FIGS. 5 to 8, the same reference numerals are assigned to the same constituent components as those in FIGS. 2 and 4, and the detailed description thereof will be omitted. In FIGS. 5 and 8, an illustration of the pressing member 54 is omitted.

FIGS. 5 to 8 are schematic views of the distal end surface 21*a* of the distal end body 21 as viewed from the optical axis direction. In addition, in FIGS. 5 to 8, thicknesses are exaggerated for illustration purposes to clearly show the receiving portion 52, the first restricting portion 56, the second restricting portion 58, and a circular arc surface 59. However, as described above, the receiving portion 52, the first restricting portion 56, the second restricting portion 58, and the circular arc surface 59 are each composed of a portion of the distal end body 21.

The disposition of the pressing member 54 is not limited to FIG. 4, and there is an allowable range for the disposition of the pressing member 54. For example, as shown in FIG. 5, the pressing member 54 may be disposed by being shifted from the first direction $D_1$.

A point at which a first straight line $L_1$ passing through the center point PL of the lens accommodating portion 40 and a position 58*a* within one of the second restricting portions 58, which is farthest from a straight line Lc passing through the center point PL of the lens accommodating portion 40 and the center point Pt of the housing 42, where the second restricting portion 58 effectively acts as a restriction for the position in the second direction $D_2$ which is the cross direction, intersects the outer edge of the lens accommodating portion 40 provided on a side opposite to the housing 42 with respect to the center point PL of the lens accommodating portion 40 is set as a first point $P_1$.

A point at which a second straight line $L_2$ passing through the center point PL of the lens accommodating portion 40 and a position 58*b* within the other of the second restricting portions 58, which is farthest from the straight line Lc passing through the center point PL of the lens accommodating portion 40 and the center point Pt of the housing 42, where the second restricting portion 58 effectively acts as a restriction for the position in the second direction $D_2$ which is the cross direction, intersects the outer edge of the lens accommodating portion 40 provided on the side opposite to the housing 42 with respect to the center point PL of the lens accommodating portion 40 is set as a second point $P_2$.

The second restricting portion 58 effectively acting as the restriction of the position in the second direction $D_2$ described above means that the clearance for the second restricting portion 58 to restrict the position of the housing 42 is sufficiently small.

Further, the position 58*a* and the position 58*b*, which are closest to the lens accommodating portion 40 side, where the second restricting portions 58 effectively act as restrictions of the positions in the second direction $D_2$, are, for example, the side end parts 40*e* of the lens accommodating portion 40, respectively.

The pressing member 54 can be provided on the outer edge of the lens accommodating portion 40, within a range $\theta_1$ between the first point $P_1$ and the second point $P_2$. The above-described range $\theta_1$ is the allowable range for the disposition of the pressing member 54.

In a case where the pressing member 54 is provided between the first point $P_1$ and the second point $P_2$ on the outer edge of the lens accommodating portion 40 described above, that is, within the range $\theta_1$ described above, the effect of suppressing the above-described drive malfunction of the lens drive unit 44 can be obtained without increasing the force acting in the second direction $D_2$. As shown in FIG. 2, it is more preferable that the pressing member 54 is disposed on the straight line Lc passing through the center point PL of the lens accommodating portion 40 and the center point Pt of the housing 42.

The first point $P_1$ and the second point $P_2$ are contact points between the pressing member 54 and the lens accommodating portion 40.

In FIG. 4 described above, the configuration is such that the receiving portion 52 and the second restricting portion 58 are spaced apart from each other, but the present invention is not limited thereto, and a configuration may be employed in which the receiving portion 52 and the second restricting portion 58 are integrally formed. In this case, for example, as shown in FIG. 6, the receiving portion 52 and the second restricting portion 58 are continuously and integrally disposed along the outer edge of the housing 42. In this case, for example, the receiving portion 52 and the second restricting portion 58 are integrally formed on the circular arc surface 59. The circular arc surface 59 can exhibit the functions of both the receiving portion 52 and the second restricting portion 58 even at a length equal to or less than half the entire circumference of the housing 42 in a case where the outer edge of the housing 42 is circular. The circular arc surface 59 has preferably a length of at least 1/12 of the entire circumference of the housing 42 in order to exhibit the functions of both the receiving portion 52 and the second restricting portion 58 in a case where the outer edge of the housing 42 is circular.

Further, by using the circular arc surface 59, the receiving portion 52 and the second restricting portion 58 can be formed together, and there is no need to separate the receiving portion 52 and the second restricting portion 58, which is also preferable in terms of processing.

In a case of the circular arc surface 59 as well, there is an allowable range for the disposition of the pressing member 54. This will be described.

As shown in FIG. 6, a point at which a first straight line $L_1$ passing through the center point PL of the lens accommodating portion 40 and one position 59*a* within the circular arc surface 59, which is farthest from the straight line Lc passing through the center point PL of the lens accommodating portion 40 and the center point Pt of the housing 42, where the circular arc surface 59 effectively acts as a restriction for the position in the second direction $D_2$, intersects the outer edge of the lens accommodating portion 40 provided on the side opposite to the housing 42 with respect to the center point PL of the lens accommodating portion 40 is set as a first point $P_1$.

A point at which a second straight line $L_2$ passing through the center point PL of the lens accommodating portion 40 and the other position 59*b* within the circular arc surface 59, which is farthest from the straight line Lc passing through the center point PL of the lens accommodating portion 40 and the center point Pt of the housing 42, where the circular arc surface 59 effectively acts as a restriction for the position in the second direction $D_2$, intersects the outer edge of the lens accommodating portion 40 provided on the side opposite to the housing 42 with respect to the center point PL of the lens accommodating portion 40 is set as a second point $P_2$.

The circular arc surface 59 effectively acting as the restriction of the position in the second direction $D_2$ described above means that the clearance for the circular arc surface 59 to restrict the position of the housing 42 is sufficiently small.

The pressing member 54 can be provided on the outer edge of the lens accommodating portion 40, within a range $\theta_1$ between the first point $P_1$ and the second point $P_2$. The above-described range $\theta_1$ is the allowable range for the disposition of the pressing member 54.

One position 59*a* of the circular arc surface 59 and the other position 59*b* of the circular arc surface 59 face each other with the straight line Lc interposed therebetween. Further, the position 59*a* of the circular arc surface 59 corresponds to the position 58*a* of the second restricting portion 58 described above. The position 59*b* of the circular arc surface 59 corresponds to the position 58*b* of the second restricting portion 58 described above.

In addition, in FIG. 4, the receiving portion 52 is provided on a housing 42 side, and the pressing member 54 is provided on the lens accommodating portion 40 side, but the present invention is not limited thereto. For example, as shown in FIG. 7, a configuration may also be employed in which the receiving portion 52 is provided on the lens accommodating portion 40 side, and the pressing member 54 is provided on the housing 42 side. In the configuration shown in FIG. 7, the pressing member 54 presses the housing 42. Further, the receiving portion 52 and the first restricting portion 56 can also be continuously and integrally disposed along the outer edge of the lens accommodating portion 40. In this case, for example, in a case where the distal end surface 21*a* of the distal end body 21 is viewed from the optical axis direction, the receiving portion 52 and the first restricting portion 56 are integrally formed on the circular arc surface.

There is an allowable range for the disposition of the pressing member 54 even in a configuration shown in FIG. 7 in which the receiving portion 52 is provided on the lens accommodating portion 40 side and the pressing member 54 is provided on the housing 42 side.

As shown in FIG. 8, a point at which a third straight line $L_3$ passing through the center point Pt of the housing 42 and a position 56*a* within one of the first restricting portions 56, which is farthest from the straight line Lc passing through the center point PL of the lens accommodating portion 40 and the center point Pt of the housing 42, where the first restricting portion 56 effectively acts as a restriction for the position in the second direction $D_2$ which is the cross direction, intersects the outer edge of the housing 42 provided on a side opposite to the lens accommodating portion 40 with respect to the center point Pt of the housing 42 is set as a third point $P_3$.

A point at which a fourth straight line $L_4$ passing through the center point Pt of the housing 42 and a position 56*b* within the other of the first restricting portions 56, which is farthest from the straight line Lc passing through the center point PL of the lens accommodating portion 40 and the center point Pt of the housing 42, where the first restricting portion 56 effectively acts as a restriction for the position in the second direction $D_2$ which is the cross direction, intersects the outer edge of the housing 42 provided on the side opposite to the lens accommodating portion 40 with respect to the center point Pt of the housing 42 is set as a fourth point $P_4$.

The first restricting portion 56 effectively acting as the restriction of the position in the second direction $D_2$ described above means that the clearance for the first restricting portion 56 to restrict the position of the lens accommodating portion 40 is sufficiently small.

Further, the position 56*a* and the position 56*b*, which are closest to the housing 42 side, where the first restricting portions 56 effectively act as restrictions of the positions in the second direction $D_2$, are, for example, the side end parts 42*e* of the housing 42, respectively.

The pressing member 54 can be provided on the outer edge of the housing 42, within a range $\theta_2$ between the third point $P_3$ and the fourth point $P_4$. The above-described range $\theta_2$ is the allowable range for the disposition of the pressing member 54.

In a case where the pressing member 54 is provided between the third point $P_3$ and the fourth point $P_4$ on the outer edge of the housing 42 described above, that is, within the range $\theta_2$ described above, the effect of suppressing the above-described drive malfunction of the lens drive unit 44 can be obtained without increasing the force acting in the second direction $D_2$.

The third point $P_3$ and the fourth point $P_4$ are contact points between the pressing member 54 and the housing 42.

The present invention is basically configured as described above. Although the endoscope imaging device and the endoscope of the embodiment of the present invention have been described in detail above, the present invention is not limited to the above-described embodiment, and various improvements or modifications may be made within a range that does not depart from the gist of the present invention, of course.

EXPLANATION OF REFERENCES

10: endoscope system
12: endoscope
12*a*: distal end portion
14: light source device
16: processor device
20: endoscope imaging device
21: distal end body
21*a*: distal end surface
21*b*: forceps port
21*c*: observation window
21*d*: light guide
23: imaging lens
25: sensor
25*a*: light-receiving surface
26: circuit board
26*a*: front surface
27: prism
27*a*: incidence surface
27*b*: emission surface
27*c*: inclined surface
27*e*: reflecting surface
28: signal cable
28*a*: signal line
28*b*: covering layer
28*c*: shield conductor
28*d*: outer sheath
29: bump
30: objective lens
30*a*, 30*b*, 30*c*, 32*a*, 32*b*, 33*a*, 33*b*, 33*c*: lens
31: first movable lens
32: second movable lens
33: stationary lens
35: lens holding member
36: first movable lens holding portion
36*a*: guide portion
36*b*: lens frame
36*c*: coupling portion
37: second movable lens holding portion
37*a*: guide portion
37*b*: lens frame
37*c*: coupling portion
38: stationary lens holding member
40: lens accommodating portion
40*a*: end surface
42*a*: end surface
40*b*: end part
40*d*: end part
40*e*, 42*e*: side end part
42: housing
42*c*: locking ring
42*d*: end part
43: coupling portion
44: lens drive unit
45: cam shaft
45*a*: distal end
45*b*: flange
45*c*: end part
46: drive member
47: distal end support portion
48: prism holding portion
49: cover glass
50, 51: electronic component
52: receiving portion
54: pressing member
56: first restricting portion

56a, 56b, 58a, 58b, 59a, 59b: position
58: second restricting portion
59: circular arc surface
C: optical axis
Cd: rotation axis
CL, Ct: central axis
$D_1$: first direction
$D_2$: second direction
$L_1$: first straight line
$L_2$: second straight line
$L_3$: third straight line
$L_4$: fourth straight line
Lc: straight line
$P_1$: first point
$P_2$: second point
$P_3$: third point
$P_4$: fourth point
PL, Pt: center point

What is claimed is:

1. An endoscope imaging device including, on a distal end side, a plurality of lenses that include a first movable lens which is movable along an optical axis direction, and a sensor that captures a subject image formed by the plurality of lenses, the endoscope imaging device comprising:

a lens accommodating portion that accommodates the first movable lens which is movable along the optical axis direction among the plurality of lenses;

a housing that is disposed alongside the lens accommodating portion as viewed from the optical axis direction;

a coupling portion that couples the lens accommodating portion and the housing to each other in a state in which the lens accommodating portion and the housing communicate with each other;

a lens drive unit that is accommodated in the housing, wherein the lens drive unit includes a movable lens holding portion that holds the first movable lens, and the movable lens holding portion is disposed across the lens accommodating portion and the housing through the coupling portion;

a receiving portion that is provided at an end part of the housing or an end part of the lens accommodating portion in an extension direction of the coupling portion as viewed from the optical axis direction;

a pressing member that is provided at the end part of the lens accommodating portion or the end part of the housing facing the receiving portion in the extension direction and presses the lens accommodating portion or the housing;

a first restricting portion that restricts a position of the lens accommodating portion in a cross direction crossing the extension direction of the coupling portion; and a second restricting portion that restricts a position of the housing in the cross direction crossing the extension direction of the coupling portion, wherein the receiving portion, the first restricting portion, and the second restricting portion are each formed as part of a distal end body that supports the lens accommodating portion and the housing, wherein the extension direction of the coupling portion is a first direction that passes through a center point of the lens accommodating portion and a center point of the housing when viewed from the optical axis direction, wherein the movable lens holding portion comprises:

a tubular guide portion accommodated in the housing;

a lens frame that holds the first movable lens and is accommodated in the lens accommodating portion; and a coupling portion that couples the tubular guide portion and the lens frame to each other, wherein the coupling portion of the movable lens holding portion passing through the coupling portion that couples the lens accommodating portion and the housing so that the first movable lens moves along the optical axis direction.

2. The endoscope imaging device according to claim 1, wherein the first restricting portion is provided on both sides of the lens accommodating portion in the cross direction.

3. The endoscope imaging device according to claim 2, wherein the pressing member is provided on an outer edge of the housing, within a range between a third point and a fourth point: the third point being, as viewed from the optical axis direction, a point at which a third straight line passing through a center point of the housing and a position within one of the first restricting portions, which is farthest from a straight line passing through a center point of the lens accommodating portion and the center point of the housing, where the first restricting portion effectively acts as a restriction for the position in the cross direction, intersects the outer edge of the housing provided on a side opposite to the lens accommodating portion with respect to the center point of the housing; and the fourth point being, as viewed from the optical axis direction, a point at which a fourth straight line passing through the center point of the housing and a position within the other of the first restricting portions, which is farthest from the straight line passing through the center point of the lens accommodating portion and the center point of the housing, where the first restricting portion effectively acts as a restriction for the position in the cross direction, intersects the outer edge of the housing provided on the side opposite to the lens accommodating portion with respect to the center point of the housing.

4. The endoscope imaging device according to claim 2, wherein the second restricting portion is provided on both sides of the housing in the cross direction.

5. The endoscope imaging device according to claim 4, wherein the pressing member is provided on an outer edge of the lens accommodating portion, within a range between a first point and a second point: the first point being, as viewed from the optical axis direction, a point at which a first straight line passing through a center point of the lens accommodating portion and a position within one of the second restricting portions, which is farthest from a straight line passing through the center point of the lens accommodating portion and a center point of the housing, where the second restricting portion effectively acts as a restriction for the position in the cross direction, intersects the outer edge of the lens accommodating portion provided on a side opposite to the housing with respect to the center point of the lens accommodating portion; and the second point being, as viewed from the optical axis direction, a point at which a second straight line passing through the center point of the lens accommodating portion and a position within the other of the second restricting portions, which is farthest from the straight line passing through the center point of the lens accommodating portion and the center point of the housing, where the second restricting portion effectively acts as a restriction for the position in the cross direction, intersects the outer edge of the lens accommodating portion provided on the side opposite to the housing with respect to the center point of the lens accommodating portion.

6. The endoscope imaging device according to claim 2, wherein the receiving portion and the second restricting portion are continuously disposed along an outer edge of the housing.

7. The endoscope imaging device according to claim 2, wherein the receiving portion and the first restricting portion are continuously disposed along an outer edge of the lens accommodating portion.

8. The endoscope imaging device according to claim 2, wherein the extension direction of the coupling portion is a first direction that passes through a center point of the lens accommodating portion and a center point of the housing, as viewed from the optical axis direction, and the cross direction is a second direction orthogonal to the first direction within the same plane, as viewed from the optical axis direction.

9. The endoscope imaging device according to claim 1, wherein the second restricting portion is provided on both sides of the housing in the cross direction.

10. The endoscope imaging device according to claim 9, wherein the pressing member is provided on an outer edge of the lens accommodating portion, within a range between a first point and a second point: the first point being, as viewed from the optical axis direction, a point at which a first straight line passing through a center point of the lens accommodating portion and a position within one of the second restricting portions, which is farthest from a straight line passing through the center point of the lens accommodating portion and a center point of the housing, where the second restricting portion effectively acts as a restriction for the position in the cross direction, intersects the outer edge of the lens accommodating portion provided on a side opposite to the housing with respect to the center point of the lens accommodating portion; and the second point being, as viewed from the optical axis direction, a point at which a second straight line passing through the center point of the lens accommodating portion and a position within the other of the second restricting portions, which is farthest from the straight line passing through the center point of the lens accommodating portion and the center point of the housing, where the second restricting portion effectively acts as a restriction for the position in the cross direction, intersects the outer edge of the lens accommodating portion provided on the side opposite to the housing with respect to the center point of the lens accommodating portion.

11. The endoscope imaging device according to claim 9, wherein the receiving portion and the second restricting portion are continuously disposed along an outer edge of the housing.

12. The endoscope imaging device according to claim 9, wherein the receiving portion and the first restricting portion are continuously disposed along an outer edge of the lens accommodating portion.

13. The endoscope imaging device according to claim 9, wherein the extension direction of the coupling portion is a first direction that passes through a center point of the lens accommodating portion and a center point of the housing, as viewed from the optical axis direction, and the cross direction is a second direction orthogonal to the first direction within the same plane, as viewed from the optical axis direction.

14. The endoscope imaging device according to claim 1, wherein the receiving portion and the second restricting portion are continuously disposed along an outer edge of the housing.

15. The endoscope imaging device according to claim 1, wherein the receiving portion and the first restricting portion are continuously disposed along an outer edge of the lens accommodating portion.

16. The endoscope imaging device according to claim 1, wherein the extension direction of the coupling portion is a first direction that passes through a center point of the lens accommodating portion and a center point of the housing, as viewed from the optical axis direction, and the cross direction is a second direction orthogonal to the first direction within the same plane, as viewed from the optical axis direction.

17. An endoscope comprising:
the endoscope imaging device according to claim 1.

18. An endoscope comprising:
the endoscope imaging device according to claim 2.

19. An endoscope comprising:
the endoscope imaging device according to claim 9.

* * * * *